United States Patent [19]

Miller et al.

[11] Plant 4,858

[45] Jun. 15, 1982

[54] CHRYSANTHEMUM PLANT

[75] Inventors: Dennis E. Miller; William E. Duffett, both of Salinas, Calif.

[73] Assignee: Yoder Brothers, Inc., Barberton, Ohio

[21] Appl. No.: 125,191

[22] Filed: Feb. 27, 1980

[51] Int. Cl.[3] ..... A01H 5/00

[52] U.S. Cl. ..... Plt./76

[58] Field of Search ..... Plt./76

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant which is a sport of the cultivar Tempo, being distinguished from its parental cultivar by its dark purple ray floret color and smaller diameter across face of inflorescence.

1 Drawing Figure

1

The present invention comprises a new and distinct cultivar of *Chrysanthemum morifolium,* Ramat., hereinafter referred to by the cultivar name Temptation.

Temptation is the product of a planned sport induction program. Temptation was discovered and selected by Dennis E. Miller and William E. Duffett on July 18, 1977 at Salinas, Calif. as a color variant within a flowering block of Tempo, U.S. plant patent pending. Plants within the flowering block were derived as cuttings from stock plants which had been exposed as unrooted cuttings to an x-ray source of 2600 r units.

The first act of asexual reproduction of Temptation was accomplished when vegetative cuttings were taken from the initial selection in October, 1978 in a controlled environment in Salinas, Calif. by a technician working under formulations established and supervised by Dennis E. Miller and William E. Duffett. Horticultural examination of selected units initiated Jan. 26, 1979 has demonstrated that the combination of characteristics as herein disclosed for Temptation are firmly fixed and are retained through successive generations of asexual reproduction.

Temptation has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Temptation which in combination distinguish this chrysanthemum as a new and distinct cultivar:

(1) flat capitulum form, (2) decorative capitulum type, (3) dark purple ray floret color, with minimal color oxidation, (4) diameter across face of capitulum ranging from 90 to 110 mm. at maturity, (5) uniform nine week photoperiodic flowering response to short days, (6) tall plant height (requiring 1-2 long day weeks prior to pinch and short days, and two applications 2500 ppm. B-9 SP 14 to 21 days after the beginning of short days to attain a flowered plant height of 30 to 45 cm.), and (7) semi-spreading branching pattern.

2

The accompanying photographic drawing shows typical inflorescence of Temptation, with the color being as nearly true as possible with illustrations of this type.

Of the many commercial cultivars known to the present inventors, the most similar in comparison to Temptation is the parental cultivar Tempo. Reference is made to attached Chart A which compares certain characteristics of Temptation to those same characteristics of Tempo. General comparisons are as follows.

In comparison to Tempo, Temptation has different ray floret color and smaller diameter across face of capitulum. The capitulum form, capitulum type, plant height, branching pattern and flowering response period of Temptation are similar to those same characteristics of Tempo.

In the following description, color references are made to The Royal Horticultural Society Colour Chart. The color values were determined between 10:00 and 10:30 a.m. on Oct. 5, 1979 under 75 foot-candle light intensity at Salinas, Calif.

Botanical classification: *Chrysanthemum morifolium,* Ramat., cv Temptation.

I. Inflorescence:

A. Capitulum:

*Form.*—Flat.

*Type.*—Decorative.

*Diameter across face.*—90 to 110 mm.

B. Corolla of ray florets:

*General tonality from a distance of three meters*.—Dark purple, approximately 60-A and 60-B oxidizing to 71-A and 71-B.

*Color (abaxial).*—Approximately 60-A and 60-B oxidizing to 71-A and 71-B.

*Color (adaxial).*—Approximately 61-A overlaid with white.

C. Reproductive organs:

*Androecium.*—Present disc florets only; scant to few; scant pollen.

*Gynoecium.*—Present both ray and disc florets.

II. Plant:

A. General appearance

*Height.*—Tall, (pot mum culture), requiring 1-2 long day weeks and 2 applications 2500 ppm. B-9 SP to attain a height as a flowering plant of 30 to 45 cm.

*Branching pattern.*—Semi-spreading.

B. Foliage:

*Color (abaxial).*—Approximately 139-A.

*Color (adaxial).*—Approximately 137-A overlaid with white.

CHART A

COMPARISON OF TEMPTATION AND TEMPO

| CULTIVAR | RAY FLORET COLOR | CAPITULUM FORM & TYPE | BRANCHING PATTERN |
|---|---|---|---|
| Temptation | Dark Purple | Flat Decorative | Semi-spreading |
| Tempo | Dark Lavender Pink | Flat Decorative | Semi-spreading |

| CULTIVAR | DIAMETER ACROSS FACE OF CAPITULUM | PLANT HEIGHT | FLOWERING RESPONSE PERIOD |
|---|---|---|---|
| Temptation | 90 to 110 mm. | Tall, 30 to 45 cm. | 9 week |
| Tempo | 110 to 130 mm. | Tall 30 to 45 cm. | 9 week |

COMPARISONS MADE OF PLANTS GROWN AS PINCHED DISBUDDED POTS IN SALINAS, CALIFORNIA

We claim:

1. A new and distinct cultivar of *Chrysanthemum morifolium,* Ramat., plant known by the cultivar name Temptation, as described and illustrated, and particularly characterized as to uniqueness by the combined characteristics of flat capitulum form; decorative capitulum type; dark purple ray floret color, with minimal color oxidation; diameter across face of capitulum ranging from 90 to 110 mm. at maturity; uniform nine week flowering response; tall plant height; and semi-spreading branching pattern.

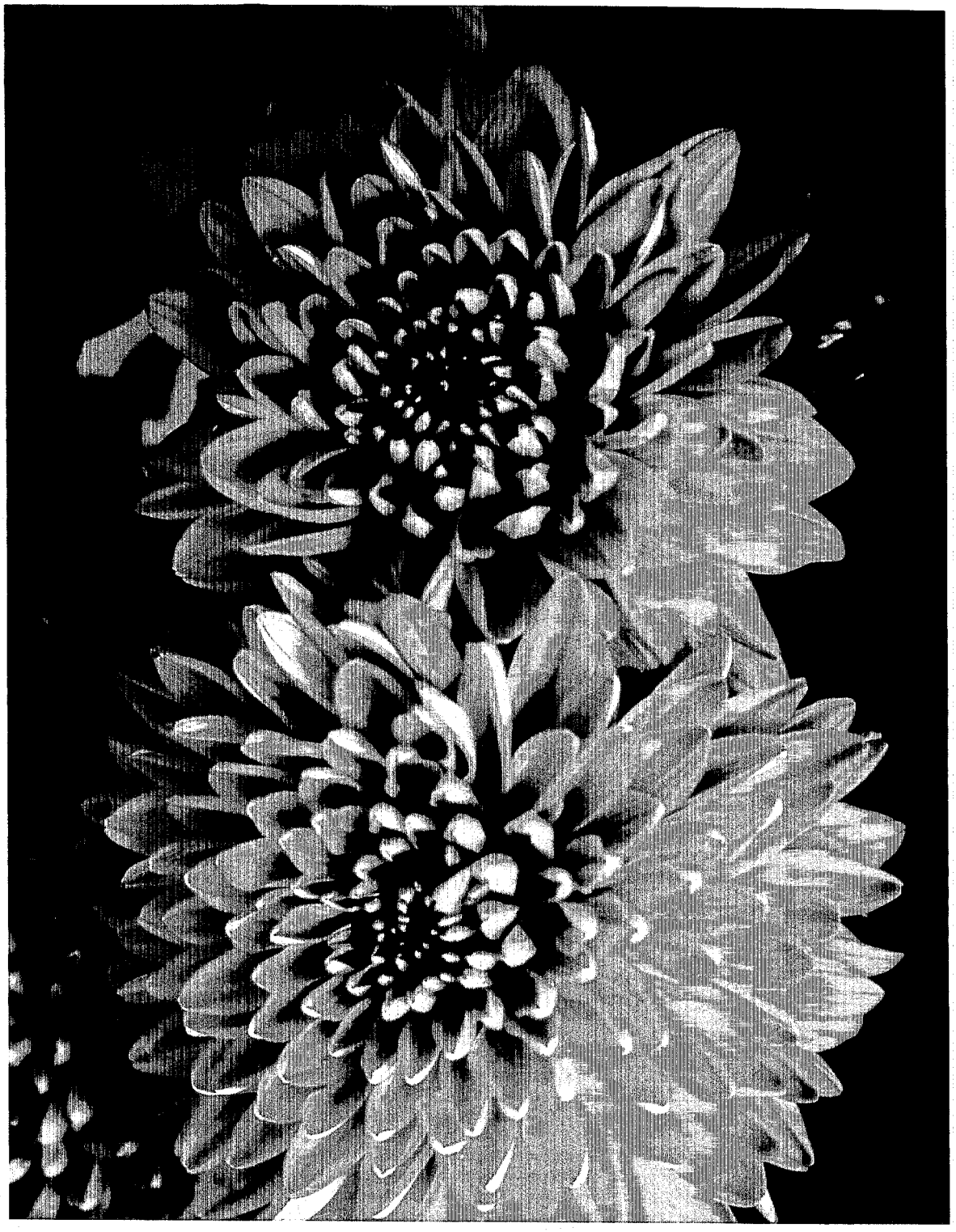

* * * * *